US005744333A

United States Patent [19]
Cociancich et al.

[11] Patent Number: 5,744,333
[45] Date of Patent: Apr. 28, 1998

[54] PROCESS FOR THE EXTRACTION OF TAXOL AND DERIVATIVES THEREOF FROM ROOTS OF PLANTS OF THE GENUS TAXUS

[75] Inventors: Ermanno Cociancich; Roberto Pace, both of Milan, Italy

[73] Assignee: Indena SPA, Milan, Italy

[21] Appl. No.: 487,919

[22] Filed: Jun. 7, 1995

Related U.S. Application Data

[63] Continuation of Ser. No. 881,504, May 11, 1992, abandoned.

[30] Foreign Application Priority Data

Jan. 31, 1992 [IT] Italy ................................. MI92A0181

[51] Int. Cl.⁶ ..................................................... C12P 17/02
[52] U.S. Cl. ........................ 435/123; 549/510; 435/430; 435/422
[58] Field of Search .................. 435/123, 41, 240.4, 435/240.6, 240.8, 430, 422; 549/510

[56] References Cited

U.S. PATENT DOCUMENTS 5,019,504 5/1991 Christen et al. ........................ 549/510
5,413,928 5/1995 Weathers ............................... 435/240.1

OTHER PUBLICATIONS

Vidensek, N. et al. "Taxol Content in Bark, Wood, Root . . . species", *J of Natural Products* vol. 53, No. 6, pp. 1609–1610, 1990.

Witherup, K. et al., "Taxus spp. Needle Contain Amounts of Toxol . . . Isolation", *J of Natural Products*, vol. 53, No. 5, pp. 1249–1255.

Gamborg, O, In Manual of Industrial Microbiology and Biotechnology, 1986, Ed. Yeumaih et al., pp. 263–268.

*Primary Examiner*—Irene Marx
*Attorney, Agent, or Firm*—Pennie & Edmonds

[57] ABSTRACT

Processes for the extraction of taxol and derivatives thereof from roots of plants of the genus Taxus are described.

13 Claims, No Drawings

PROCESS FOR THE EXTRACTION OF TAXOL AND DERIVATIVES THEREOF FROM ROOTS OF PLANTS OF THE GENUS TAXUS

This application is a continuation of Ser. No. 07/881,504, filed May 11, 1992, now abandoned.

The present invention pertains to the use of roots of plants of the genus Taxus for the production of taxol, of intermediates useful for the synthesis of taxol and of derivatives thereof.

An important problem hindering the clinical development of taxol, a promising anticancer drug of vegetable origin, is the low content of this terpenoid in the Taxus species presently known to be a source for its extraction and isolation. To date, taxol has been isolated from the bark of *T. brevifolia*, which is a spontaneous species present in the North American forests and, in lower amounts, from the bark and aerial parts of other Taxus species.

Moreover, the isolation of highly pure taxol from these vegetable sources requires cumbersome purification steps because of the presence in the extracts of several other structurally related terpenoid constituents, which are difficult to separate from taxol.

The bark of *T. brevifolia*, which is the most abundant source found to date, contains about 0.02–0.03% of taxol, whereas the roots contain less than 0.01% (*Journal of Natural Products*, 53, 1609–10, 1990).

However, the removal of the bark causes the death of the plants of this species, with serious environmental consequences due to the very slow growth of these species. As a consequence, the future availability of the active principle is put at risk.

For these reasons, the above cited species of Taxus are protected everywhere and special regulations recently have been enacted in the United States of America, where taxol was discovered, in order to prevent the extinction of the plant.

It now has been found that taxol is present in concentrations ranging from 0.08% to 0.15% w/w in the roots of *T. media* "Hicksii" (Rehder) (synonyms: *T. cuspidata hicksii* Hort or *T. hicksii* Hort—female plant) or of *T. media* "Hill" (synonyms: *T. cuspidata columnaris* Hort; *T. nana pyramidalis hilli* Hort), disclosed in "Study of the Genus Taxus", *Ohio Agricult. Research & Development Center Bull.* No. 1086 5/1976, and that the structurally related baccatin-III and 10-desacetylbaccatin-III are present in the same species at concentrations ranging from 0.02% to 0.06% w/w and from 0.03% to 0.08% w/w, respectively.

The taxol content in the roots of these species is at least 4-times higher than that found in the prior-art sources.

Similar concentrations were found in the plant *T. media* dark green spreader. In contrast to the spontaneous species, these plants can be easily cultivated since they were originally selected for ornamental purposes. Cultivation provides a constant availability of the vegetable source which can be planned to accommodate the production requirements for the active principles.

The invention therefore relates to a process for the extraction of taxol and of other structurally related terpenoids from a vegetable source belonging to the Taxus genus, characterized by using, as a vegetable source, roots or in vitro cultures of roots of a plant selected from *T. media* "Hicksii", *T. media* "Hill" and *T. media* dark green spreader.

More particularly, the process of the invention allows one to obtain, in economically advantageous amounts, taxol, baccatin-III and 10-desacetyl-baccatin-III, having the following formulae:

(1) Taxol: $R_1 = $ $R_2 = Ac$ (2) Baccatin-III: $R_1 = H$, $R_2 = Ac$ (3) 10-Desacetylbaccatin-III: $R_1 = R_2 = H$ Baccatin-III and 10-desacetylbaccatin-III can be used as intermediates for the synthesis of taxol.

For industrial applications, the plants can be propagated by cutting. The plant can be used as an extraction source after 3 years from the field transplant, without any particular limitation.

Starting from the third year the weight ratio of the aerial part to roots is optimal for extractive purposes.

The plant can be grown in a greenhouse or, preferably, in an open field where it should be kept under maximum light exposure, preferably at an altitude from 500 to 2500 m. The roots with a 5 cm trunk portion are used, and are dried immediately after harvesting in a forced air drier at a temperature from 30° to 60° C.

The plant also can be micropropagated using, as explants, young shoots or buds from material which can optionally be subjected to a treatment to restore to juvenile form (cutting, grafting or layering).

The seedlings obtained by this process, after a short period in a greenhouse, are placed in an open field according to the methods already described for cuttings.

Root cultures having a higher content of taxol and its derivatives than that usually found in nature were produced in a fermenter from root explants, which have been sterilized according to conventional methods for in vitro cultures.

These cultures were induced and stabilized on culture media containing nutritive and hormonal factors, according to conventional techniques.

The vegetable material obtainable from said cultures or from integral roots is subjected, according to the invention, to suitable extractive processes. For instance, the vegetable material, suitably dried and ground, may be extracted with protic solvents (preferably lower alcohols such as methanol or ethanol) or medium polarity aprotic solvents such as acetone or ethyl acetate.

The extracts, after water dilution, are concentrated and the desired compounds are separated by extraction with a water immiscible solvent, such as methylene chloride, chloroform, or ethyl acetate. After evaporating the organic extracts under reduced pressure, the residue may be purified by conventional methods such as chromatographic techniques, crystallization, lyophilization, and combinations thereof.

In the following examples, an analysis of the terpenoids in the vegetable material, an isolation process of said terpenoids from integral roots, and methods for the micropropagation and the in vitro culture of roots, are described.

3

The following examples will serve to further typify the nature of this invention but should not be construed as a limitation on the scope thereof, which is defined solely by the appended claims.

EXAMPLE 1

Analytical Method for the Determination of the Taxol (1), Baccatin-III (2) and 10-Desacetylbaccatin-III (3) Content in the Vegetable Material The taxol, 10-desacetylbaccatin-III and baccatin-III content is determined by HPLC analysis. A liquid chromatograph with a Brownlee—Labs Phenyl Spheric 5μ steel column (4.6 mm×250 mm) is used. The eluent is a water/acetonitrile mixture containing increasing amounts of methanol. The flow is 1 ml/minute at linear gradient monitoring the separation at 227 nm.

EXAMPLE 2

Preparation of (1), (2) and (3) from *T. cuspidata hicksii* Roots 1 kg of *T. cuspidata hicksii* roots, dried and finely ground, are extracted with methanol at room temperature.

The extract is concentrated under vacuum, diluted with water, purified by extraction with cyclohexane and treated with methylene chloride.

The organic phase is separated, evaporated to dryness.

The residue is chromatographed on a 250 g silica gel column eluting with 7:3 cyclohexane: μ ethyl acetate.

From the taxol (1) containing fractions, 1.1 g of (1), m.p. 211°–214° C., is obtained after crystallization from aqueous methanol. After subsequent elution with 1:1 cyclohexane: p ethyl acetate, crude baccatin-III (2) is obtained, which is crystallized from chloroform to yield 0.45 g of the compound, m.p. 236°–238° C. By further elution with 3:7 cyclohexane: μ ethyl acetate, the fraction containing 10-desacetylbaccatin-III (3) is obtained, which is crystallized from aqueous acetone, (0.6 g, m.p. 224°–226° C.).

EXAMPLE 3

Preparation of Plantules from Explants of *Taxus cuspidata hicksii* Hort Useful for the Micropropagation Cultures of calli of *Taxus cuspidata hicksii* Hort are induced starting from axenic plantules, on Murishige-Skoog medium with added auxins (2.4 D,NNA) and cytokinins (kinetin) at a concentration of 2.5 mg/l in an auxin/cytokinin 2:1 ratio. Liquid substrate cell cultures are prepared from the so obtained calli, under the above described conditions for the production of calli. After 10 day incubation the cultures are mixed with cadmium sulfate at a concentration of 200 μM and then incubated under the same conditions (rotative stirring 100 rpm, temperature 25° C., light 3000 Lux).

Cells from this culture, placed on agar and nutritive solution, generate calli which after 20 days give rise to plantules which may be transferred into a greenhouse.

EXAMPLE 4

Production of *Taxus cuspidata hicksii* Hort Roots by Tissue Culture

Roots of *Taxus cuspidata hicksii* Hort are induced from leaves previously sterilized with 1% sodium hypochlorite for 3 minutes, and transformed with *Agrobacterium rhizogenes* 15834. The obtained cultures are transferred by serial passages onto Murishige-Skoog medium without hormones and with a carbon source (saccharose) at a concentration of 22% w/w and incubated for 15 days at 100 rpm in the dark.

After addition of heavy metals at a concentration of 200 μM, the root cultures are incubated for 10 more days and then homogenized and extracted for the isolation of taxol according to the process of Example 2.

What is claimed is:

1. A process for isolating taxol from plants of the genus Taxus, which comprises:

cultivating a species of Taxus selected from the group consisting of *T. media* "Hicksii", *T. media* "Hill" and *T. media* "dark green spreader", for a time sufficient to obtain plant roots having a concentration of taxol of from about 0.08% to 0.15% (w/w), and either a concentration of baccatin-III of from about 0.02% to 0.06% (w/w) or a concentration of 10-desacetylbaccatin-III of from about 0.03% to 0.08% (w/w);

harvesting the plant-roots;

extracting a mixture of taxol and either baccatin-III or 10-desacetylbaccatin-III in said amounts from the plant roots; and isolating the taxol from the extracted mixture.

2. The process according to claim 1, wherein taxol and baccatin-III or 10-desacetylbaccatin-III are extracted from the plant roots with a solvent.

3. The process according to claim 2, wherein taxol and baccatin-III or 10-desacetylbaccatin-III are extracted with methanol, ethanol, acetone or ethyl acetate.

4. The process according to claim 1, wherein the plants are grown at an altitude from 500 to 2500 m for at least three years before obtaining the roots for extraction.

5. The process according to claim 3, wherein plant roots which include 5 cm trunk portions are harvested for the extraction, and are dried after harvesting at a temperature from 30° to 60° C. before extraction.

6. A process for isolating taxol from plants of the genus Taxus, which comprises;

cultivating a species of Taxus selected from the group consisting of *T. media* "Hicksii", *T. media* "Hill" and *T. media* "dark green spreader" by propagating a field transplant for at least three years to obtain plant roots having a concentration of taxol of from 0.08% to 0.15% (w/w), and a concentration of baccatin-III of from 0.02% to 0.06% (w/w) or a concentration of 10-desacetylbaccatin-III of from 0.03% to 0.08% (w/w);

harvesting the plant roots;

extracting a mixture of taxol and either baccatin-III or 10-desacetylbaccatin-III in said amounts from the plant roots; and isolating the taxol from the extracted mixture.

7. The process according to claim 6, wherein the plants are grown at an altitude from 500 to 2500 m in a greenhouse.

8. The process according to claim 6, wherein the plants are grown at an altitude from 500 to 2500 m in an open field.

9. The process according to claim 6, wherein plant roots which include 5 cm trunk portions are harvested for the extraction.

10. The process according to claim 6, wherein the plant roots are dried after harvesting at a temperature from 30° to 60° C.

11. The process according to claim 6, wherein taxol and baccatin III or 10-desacetylbaccatin-III are extracted with methanol, ethanol, acetone or ethyl acetate.

12. A process for isolating taxol from plants of the genus Taxus, which comprises;

cultivating a species of Taxus selected from the group consisting of T. media "Hicksii", T. media "Hill" and T. media "dark green spreader" by micropropagating explants of young shoots or buds to form seedlings;

maintaining the seedlings in a greenhouse to initiate growth and thereafter placing the seedlings in an open field under sufficient light exposure to encourage further growth and to provide plant roots having a concentration of taxol of from about 0.08% to 0.15% w/w, and a concentration of baccatin-III of from about 0.02% to 0.06% w/w or a concentration of 10-desacetylbaccatin-III of from about 0.03% to 0.08% w/w;

harvesting the plant-roots;

extracting a mixture of taxol and either baccatin-III or 10-desacetylbaccatin-III in said amounts from the plant roots; and isolating the taxol from the extracted mixture.

13. The process according to claim 12, wherein taxol and baccatin-III or 10-desacetylbaccatin-III are extracted with methanol, ethanol, acetone or ethyl acetate from the plant roots.

* * * * *